United States Patent
Fukuda

(10) Patent No.: US 10,816,558 B2
(45) Date of Patent: Oct. 27, 2020

(54) ELECTRODE AND BIOSENSOR FOR MEASURING ASCORBIC ACID

(71) Applicant: ARKRAY, Inc., Kyoto (JP)

(72) Inventor: Kazuo Fukuda, Kyoto (JP)

(73) Assignee: ARKRAY, Inc., Kyoto (JP)

(*) Notice: Subject to any disclaimer, the term of this patent is extended or adjusted under 35 U.S.C. 154(b) by 227 days.

(21) Appl. No.: 16/168,600

(22) Filed: Oct. 23, 2018

(65) Prior Publication Data

US 2019/0120861 A1 Apr. 25, 2019

(30) Foreign Application Priority Data

Oct. 25, 2017 (JP) ................. 2017-205759

(51) Int. Cl.
  *C12Q 1/26* (2006.01)
  *G01N 27/327* (2006.01)
  *G01N 33/82* (2006.01)
  *C12Q 1/00* (2006.01)

(52) U.S. Cl.
  CPC ............. *G01N 33/82* (2013.01); *C12Q 1/005* (2013.01); *C12Q 1/26* (2013.01); *G01N 27/327* (2013.01); *G01N 2333/902* (2013.01)

(58) Field of Classification Search
  CPC ................. G01N 33/82; G01N 27/327; G01N 2333/902; C12Q 1/005; C12Q 1/26
  See application file for complete search history.

(56) References Cited

U.S. PATENT DOCUMENTS

| 5,958,199 A | 9/1999 | Miyamoto et al. |
| 6,071,392 A * | 6/2000 | Yamamoto ............. C12Q 1/005 204/403.08 |
| 2005/0118671 A1 | 6/2005 | Bernhardt et al. |

FOREIGN PATENT DOCUMENTS

| EP | 1612275 A1 | 1/2006 |
| EP | 2623974 A1 | 8/2013 |
| JP | H09-243591 A | 9/1997 |
| JP | 2005-517926 A | 6/2005 |

OTHER PUBLICATIONS

Extended European Search Report issued in corresponding European Patent Application No. 18202621.1 dated Feb. 22, 2019.
Sortino et al., "Novel Self-Assembled Monolayers of Dipolar Ruthenium (III/II) Pentaammine (4,4'-bipyridinium) Complexes on Ultrathin Platinum Films as Redox Molecular Switches," Journal of the American Chemical Society, 125(5): 1122-1123 (2003).
Wu et al., "Amperometic determination of ascorbic acid on screen-printing ruthenium dioxide electrode," Electrochemistry Communications, 2: 90-93 (2000).

* cited by examiner

*Primary Examiner* — Jennifer Wecker
*Assistant Examiner* — Michael Paul Shimek
(74) *Attorney, Agent, or Firm* — Morgan, Lewis & Bockius LLP

(57) ABSTRACT

An ascorbic acid responsive electrode comprising an electrode, and a detection layer comprising a non-catalytic electron acceptor that receives an electron from ascorbic acid, an amino acid, and a saccharide and/or a soluble protein; wherein in the detection layer the electron acceptor is reduced by the ascorbic acid, and the reduced electron acceptor is oxidized at the electrode.

11 Claims, 7 Drawing Sheets

ELECTRODE AND BIOSENSOR FOR MEASURING ASCORBIC ACID

TECHNICAL FIELD

The present invention relates to an electrode and a biosensor for measuring the concentration of ascorbic acid in a sample, particularly to an electrode and a biosensor for measuring a high concentration ascorbic acid.

BACKGROUND ART

Ascorbic acid (vitamin C) is ingested with meals, absorbed from the small intestine, and widely distributed in organs and tissues in the body. Biochemically, it is involved in the synthesis of collagen, the synthesis of carnitine, the synthesis of adrenocortical hormone, the synthesis of catecholamine, the decomposition of lipid peroxide, the decomposition of active oxygen, etc., and plays an important role in the living body. In recent years, due to strong reducing performance of vitamin C, the anticancer effect, the immunity enhancing effect, the skin beautifying, or whitening effect have been attracting attention, and an instillation therapy with high concentration vitamin C etc. has been actually applied.

Examples of measurement of ascorbic acid include measurement for diagnosis of ascorbic acid deficiency, and measurement of ascorbic acid in food. In the case of the instillation therapy with high concentration vitamin C, real-time monitoring of the vitamin C concentration in blood is indispensable, and in the case of a blood glucose self-monitoring in diabetes, ascorbic acid in blood affects the glucose measurement value, and therefore it has been pointed out that the glucose value needs to be corrected depending on a measured value of the concentration of ascorbic acid.

Patent Document 1 discloses a method by which ascorbic acid is measured as a micronutrient in foods by a high-performance liquid chromatography (HPLC).

Patent Document 2 discloses, as an example of ascorbic acid measurement, a biosensor having an electrode including as a constituent element a detection layer including an ascorbate oxidase and an electron mediator such as a ferricyan compound.

PATENT DOCUMENTS

Patent Document 1: JP 2005-517926 A
Patent Document 2: JP 09-243591 A

SUMMARY OF INVENTION

With respect to a measurement of ascorbic acid by a high-performance liquid chromatography (HPLC) in the Patent Document 1, there is a drawback in cost, since the apparatus becomes expensive. Further, HPLC apparatus is usually installed in a large medical institution or test center, but in a facility not equipped with the apparatus, a real-time measurement is not possible due to unavoidable outsourced analysis, which is unfavorable because a real-time measurement is essential especially for an instillation therapy with high concentration vitamin C from the viewpoint of the influence of metabolism and excretion of vitamin C.

The method according to the Patent Document 2 is simple and real-time measurement is possible owing to a biosensor, however there has been a problem of deterioration of measurement accuracy due to a nonspecific catalytic reaction by reason of use of an enzyme catalyst such as an ascorbate oxidase. Further, since the storage stability of the sensor is poor due to denaturation of the enzyme, there has been a drawback in that the amount of the enzyme used needs to be increased and therefore the cost becomes higher.

In view of the above, one aspect of the present invention is to provide a biosensor which can allow accurate and simple real-time measurement of ascorbic acid at low cost.

The inventors have studied intensively and developed an ascorbic acid responsive electrode that is able to measure ascorbic acid easily and accurately without using any of HPLC and an enzyme catalyst such as an ascorbate oxidase, which have been used conventionally.

It is provided an ascorbic acid responsive electrode comprising an electrode, and a detection layer comprising a non-catalytic electron acceptor which is in contact with the electrode and receives an electron from ascorbic acid, an amino acid and a saccharide and/or a soluble protein, wherein in the detection layer the electron acceptor is reduced by the ascorbic acid, and the reduced electron acceptor is oxidized by the electrode.

It is also provided a biosensor comprising a substrate, and the ascorbic acid responsive electrode as described above and a counter electrode provided on the substrate.

It is also provided a method for measuring a concentration of ascorbic acid, comprising reacting a sample containing ascorbic acid with the biosensor as described above, applying an oxidation potential to the ascorbic acid responsive electrode to measure a response current, and calculating the concentration of ascorbic acid based on the response current.

It is also provided the method as described above, wherein said sample has the concentration of ascorbic acid of 50 mg/dL or more.

It is also provided the method as described above, wherein the concentration of ascorbic acid is calculated based on a calibration curve between the response current value and the concentration of ascorbic acid.

It is also provided a measuring apparatus comprising the biosensor as described above, a control unit for controlling voltage application to the biosensor, a detecting unit for detecting an ascorbic acid response current generated by applying a voltage to the biosensor, an arithmetic unit for calculating the concentration of ascorbic acid from the current value, and an output unit for outputting the calculated concentration of ascorbic acid.

The "electron acceptor" means a compound capable of receiving an electron from a compound having a function of an electron donor capable of giving an electron. The "non-catalytic" means not having a function of a biocatalyst for catalyzing a chemical reaction as in the case of an enzyme or an organelle, or with only a weak function of biocatalyst. Ascorbic acid has a strong function of an electron donor as a reducing substance. By utilizing this characteristic, transfer of an electron from ascorbic acid to an electron acceptor has been realized. Furthermore, since an electron acceptor that has received an electron from an electron donor becomes a reductant, it can electrochemically cause an oxidizing reaction on an electrode. Furthermore, by adding an appropriate amount of an amino acid and a saccharide and/or a soluble protein to the detection layer in addition to the electron acceptor, it becomes possible to control an excessive reaction rate to be generated in a reaction system comprising only an electron acceptor. By the above means, the linearity and reproducibility of the sensor performance in the high concentration range of ascorbic acid may be dramatically improved.

An ascorbic acid responsive electrode according to one aspect of the present invention does not use an enzyme, therefore deterioration of measurement accuracy due to a nonspecific catalytic reaction may be suppressed, and a high accuracy measurement of ascorbic acid is possible. Also, since there is no problem of storage stability caused by denaturation of an enzyme protein, the cost can be suppressed. Furthermore, by reacting an electron acceptor with ascorbic acid in the presence of an appropriate amount of an amino acid and a saccharide and/or a soluble protein, it is possible to perform a measurement with high accuracy even in a high concentration range of ascorbic acid. Therefore, it has become possible to carry out a real-time measurement of ascorbic acid accurately and simply at low cost.

Figure 1:
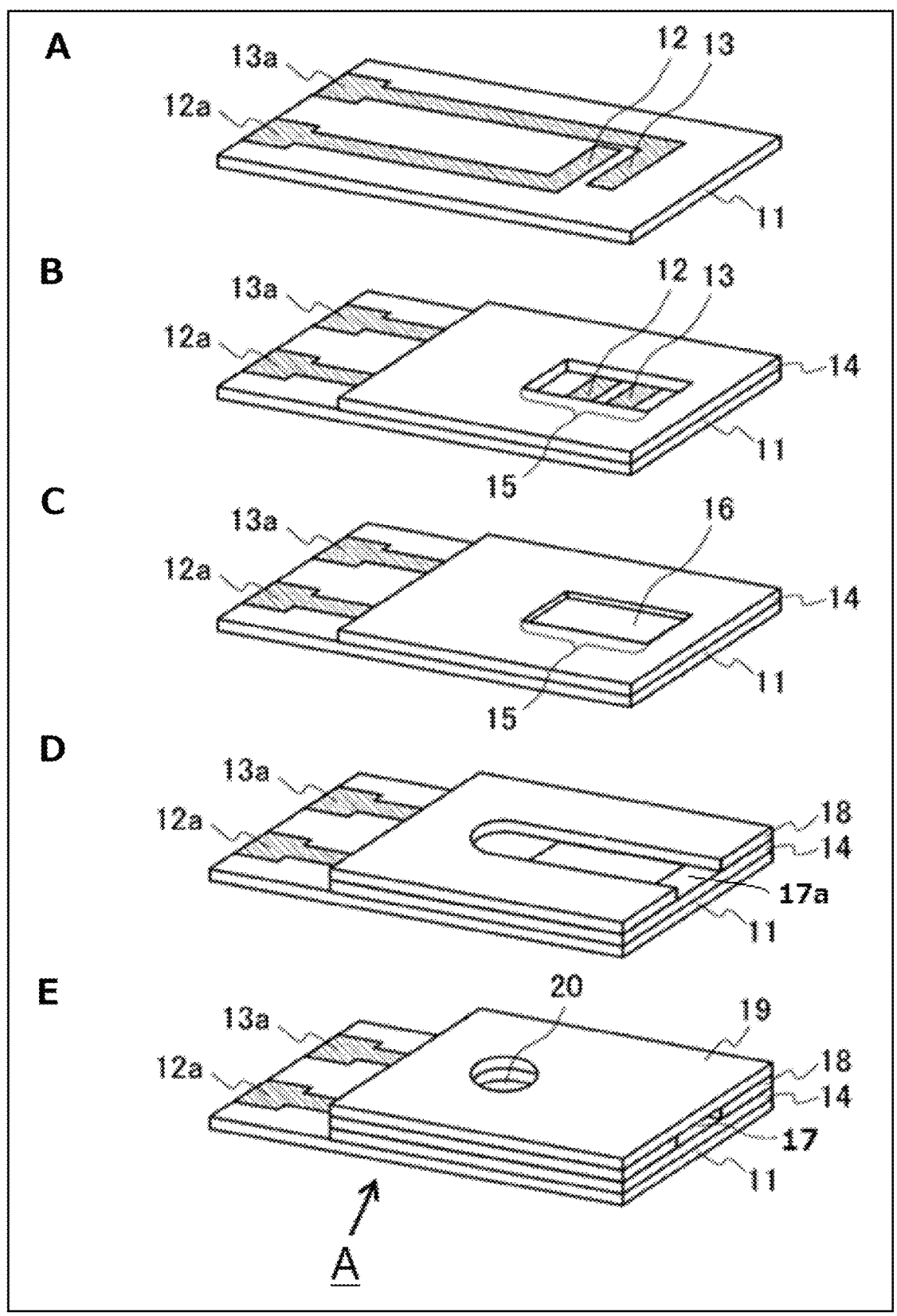
FIG. 1 is a process chart showing an example of a method of producing a biosensor of one embodiment of the present invention, Panels A to E represent schematic diagrams of a biosensor at respective steps.

EMBODIMENTS FOR CARRYING OUT THE INVENTION (Configuration of Electrode)

An ascorbic acid responsive electrode according to one embodiment of the present invention comprises an electrode, and a detection layer comprising a non-catalytic electron acceptor that receives an electron from ascorbic acid, an amino acid, and a saccharide and/or a soluble protein; wherein in the detection layer the electron acceptor is reduced by the ascorbic acid, and the reduced electron acceptor is oxidized at the electrode.

Unlike the conventional enzyme electrode in which a detection layer contains an enzyme and an electron acceptor, in an ascorbic acid responsive electrode according to one embodiment of the present invention, the detection layer contains an electron acceptor, but not an enzyme.

(Electrode)

There is no particular restriction on the material of an electrode, insofar as it is an electron-conductive material, and, for example, the electrode may be composed of a metal material, such as gold (Au), platinum (Pt), silver (Ag), or palladium (Pd), or a carbon material as represented by carbon, such as graphite, carbon nanotube, graphene, or mesoporous carbon. The electrode is formed, for example, on an insulating substrate. The insulating substrate is made of an insulating material, such as a thermoplastic resin, e.g., polyetherimide (PEI), polyethylene terephthalate (PET), or polyethylene (PE), various resins (plastics), e.g., a polyimide resin, or an epoxy resin, glass, ceramic, or paper. The size or thickness of the electrode and the insulating substrate may be selected appropriately.

(Electron Acceptor)

There is no particular restriction on an electron acceptor, insofar as it is a non-catalytic compound which is reduced by receiving an electron from ascorbic acid, and is reoxidized at the electrode. Examples thereof include a ruthenium compound, potassium ferricyanide, cytochrome c, pyrroloquinoline quinone (PQQ), $NAD^+$, $NADP^+$, a copper complex, phenazine methosulfate, and a derivative thereof, and an osmium complex, which may be used singly, or in combination of two or more thereof.

Among them, a complex composed of an oxidized metal atom and a ligand is preferable, and an oxidized ruthenium complex composed of trivalent ruthenium (Ru(III)) and ligands is more preferable.

As an electron acceptor to be used in the present invention, one synthesized by a usual organic synthetic chemical technique, or a commercially available one may be used.

(Oxidized Ruthenium Complex)

Examples of the ligand of an oxidized ruthenium complex include a nitrogen-containing ligand, such as ammonia, bipyridine, imidazole, an amino acid, phenanthroline, ethylenediamine, and a halogen ligand. These may be used in combination as mixed ligands.

An oxidized ruthenium complex serving as an electron acceptor may be contained in a detection layer in the form of a salt or the like to form a reactive complex before and/or during the reaction. Such a form is also included in embodiments of the present invention.

Preferable examples of a ruthenium ammonia complex include the following compounds, $[Ru(NH_3)_5X]^{n+}$, wherein X may be, for example, $NH_3$, a halogen, CN, pyridine, nicotinamide, bipyridine, or $H_2O$. Among these, $NH_3$, or a halogen (such as Cl, F, Br, or I) is preferable. In the Formula, n+ represents the valence of an oxidized ruthenium (III) complex, and is appropriately decided depending on the kind of X.

Examples of a bipyridine ruthenium complex include [Ru(bipyridine)$_3$],
[Ru(4,4'-dimethyl-2,2'-bipyridine)$_3$], [Ru(4,4'-diphenyl-2,2'-bipyridine)$_3$]
[Ru(4,4'-diamino-2,2'-bipyridine)$_3$], [Ru(4,4'-dihydroxy-2,2'-bipyridine)$_3$],
[Ru(4,4'-dicarboxy-2,2'-bipyridine)$_3$], [Ru(4,4'-dibromo-2,2'-bipyridine)$_3$],

[Ru(5,5'-dimethyl-2,2'-bipyridine)$_3$], [Ru(5,5'-diphenyl-2,2'-bipyridine)$_3$],
[Ru(5,5'-diamino-2,2'-bipyridine)$_3$], [Ru(5,5'-dihydroxy-2,2'-bipyridine)$_3$],
[Ru(5,5'-dicarboxy-2,2'-bipyridine)$_3$], and [Ru(5,5'-dibromo-2,2'-bipyridine)$_3$].

Examples of an imidazole ruthenium complex include [Ru(imidazole)$_6$],
[Ru(4-methyl-imidazole)$_6$], [Ru(4-phenyl-imidazole)$_6$], [Ru(4-amino-imidazole)$_6$],
[Ru(4-hydroxy-imidazole)$_6$], [Ru(4-carboxy-imidazole)$_6$], and
[Ru(4-bromo-imidazole)$_6$].

The content of an electron acceptor in a detection layer may be appropriately selected depending on the type of the measurement sample or the like, but is preferably from 0.1 µmol to 50 µmol per 1 cm$^2$ of the surface area of the detection layer, more preferably from 0.1 µmol to 10 µmol, and particularly preferably from 0.1 µmol to 5 µmol.

Although there is no particular restriction on the content of an electron acceptor in an electrode reagent (solution for preparing a detection layer), it is, for example, from 1.5 to 10% by mass, and preferably from 2.5 to 5% by mass.

(Amino Acid, Saccharide, and Soluble Protein)

In an ascorbic acid responsive electrode according to one embodiment of the present invention, in the detection layer, an electron acceptor receives an electron from ascorbic acid contained in a sample to be reduced, and the reduced electron acceptor is reoxidized at the electrode.

In doing so, the dissolving rate of a reagent (particularly an electron acceptor) to a sample solution may be regulated by inclusion of a combination of an amino acid, and a saccharide, a combination of an amino acid, and a soluble protein, or a combination of an amino acid, a saccharide, and a soluble protein in the detection layer, so that an oxidation-reduction reaction rate may be regulated. Therefore, it is possible to maintain good linearity up to a high concentration range of ascorbic acid.

Further, when a combination of an amino acid, a saccharide, and/or a soluble protein is included in the detection layer, the dissolution rate of a reagent between the sensors becomes uniform, so that high reproducibility in a high concentration range can be obtained.

There is no particular restriction on an amino acid, insofar as it is highly soluble, and may be combined with the above components so that the regulation of the dissolving rate of the reagent, and the regulation of the oxidation-reduction reaction rate may be possible. In this regard, the amino acid includes an aminosulfonic acid as represented by taurine besides an aminocarboxylic acid.

Examples of an amino acid include an aliphatic amino acid, such as glycine, and alanine; an aromatic amino acid, such as phenylalanine; an imino acid, such as proline; an oxyamino acid, such as serine and threonine; a sulfur-containing amino acid, such as cysteine, methionine, and taurine; a branched chain amino acid, such as valine, leucine, and isoleucine; an acidic amino acid, such as aspartic acid, and glutamic acid; an acidic amino acid amide, such as asparagine, and glutamine; a basic amino acid, such as lysine, and arginine; and a heterocyclic amino acid, such as tryptophan, and histidine, or a salt thereof (for example, sodium glutamate), and an aliphatic amino acid, an oxyamino acid, a sulfur-containing amino acid, and an acidic amino acid salt are preferable. These may be used singly, or in combination of two or more kinds thereof.

Although the content of an amino acid in a detection layer may be appropriately selected depending on the type of a measurement sample, or the like, it is preferably from 1 µmol to 100 µmol, more preferably from 10 µmol to 50 µmol, and particularly preferably from 10 µmol to 15 µmol, per 1 cm$^2$ of the surface area of the detection layer.

Although there is no particular restriction on the content of an amino acid in an electrode-preparing reagent, it is, for example, from 2.5 to 5.0 mass-%, and preferably from 4.5 to 5.0 mass-%.

There is no particular restriction on a saccharide, insofar as it is highly soluble, and capable of regulation of the dissolving rate and regulation of the oxidation-reduction reaction rate by combination with an amino acid. Examples thereof include a monosaccharide, a disaccharide, an oligosaccharide, a polysaccharide, a sugar alcohol, and an amino sugar, and a disaccharide, and a sugar alcohol are preferable.

Examples of a monosaccharide include glucose, fructose, mannose, galactose, xylose, and arabinose. Examples of a disaccharide include trehalose, kojibiose, nigerose, maltose, isomaltose, lactose, and sucrose. Examples of an oligosaccharide include dextrin, a galacto-oligosaccharide, and a fructo-oligosaccharide. Examples of a sugar alcohol include sorbitol, xylitol, erythritol, mannitol, and maltitol. These may be used singly, or in combination of two or more kinds thereof.

Although the content of a saccharide in a detection layer may be appropriately selected depending on the type of a measurement sample, or the like, it is preferably from 1 µmol to 100 µmol, more preferably from 1 µmol to 50 µmol, and particularly preferably from 1 µmol to 10 µmol, per 1 cm$^2$ of the surface area of the detection layer.

Although there is no particular restriction on the content of a saccharide in an electrode-preparing reagent, it is, for example, from 1.2 to 2.5 mass-%, and preferably from 2.4 to 2.5 mass-%.

There is no particular restriction on a soluble protein, insofar as it is highly soluble, capable of regulation of the dissolving rate of the reagent, and regulation of the oxidation-reduction reaction rate by combination with an amino acid, and also soluble in an aqueous solvent. Examples thereof include Neo Protein Saver (NPS) (TOYOBO CO., LTD.) derived from a silk protein, albumin, which is a serum component of bovine, human, etc., and a protein soluble in an aqueous solvent, such as casein, gelatine, etc. These may be used singly, or in combination of two or more kinds thereof. There is no particular restriction on the molecular weight of the soluble protein, ant it may be, for example, from about 1,000 to 100,000 Da.

Although the content of a soluble protein in a detection layer may be appropriately decided depending on the type of a measurement sample or the like, it is preferably from 0.1 nmol to 50 nmol, more preferably from 10 nmol to 50 nmol, and particularly preferably from 10 nmol to 30 nmol, per 1 cm$^2$ of the surface area of the detection layer.

Although there is no particular restriction on the content of a soluble protein in an electrode-preparing reagent, it is, for example, from 1.2 to 2.5 mass-%, and preferably from 2.4 to 2.5 mass-%.

As an amino acid, a saccharide, and a soluble protein to be used in the present invention, ones synthesized by a usual organic synthetic chemical technique, or commercially available ones may be used.

The content ratio (mass ratio) of an amino acid to a saccharide in an electrode is usually from 5/1 to 1/1, and preferably from 2.5/1 to 1/1.

The content ratio (mass ratio) of an amino acid to a soluble protein in an electrode is usually from 5/1 to 1/1, and preferably from 2.5/1 to 1/1.

The content ratio (mass ratio) of an electron acceptor to an amino acid in an electrode is usually from 1/5 to 1/1, and preferably from 2/3 to 1/2.

In an electrode preparing process, a solution for preparing a detection layer may be prepared as an ink suitable for screen printing containing an electron acceptor, an amino acid, a saccharide, a soluble protein, and a solvent or a dispersion medium; and the electrode preparing efficiency may be improved and the deviation between sensors may be reduced by forming an electrode by conducting patterning by printing on a substrate made of a resin or the like by a screen printing technique.

A detection layer may contain additionally a buffer and an additive such as a surfactant, and the content thereof may be selected appropriately.

As a buffer an amine-based buffer is preferable, and examples thereof include Tris, ACES, CHES, CAPSO, TAPS, CAPS, Bis-Tris, TAPSO, TES, Tricine, and ADA. These substances may be used singly or in combination of two or more kinds thereof. As the buffer, a buffer having a carboxyl group may also be used, and examples thereof include an acetic acid-sodium acetate buffer, a malic acid-sodium acetate buffer, a malonic acid-sodium acetate buffer, and a succinic acid-sodium acetate buffer.

As a surfactant, Triton X-100, CHAPS, sodium dodecyl sulfate, perfluorooctane sulfonic acid, or sodium stearate may be included.

Additional examples thereof may include an alkylaminocarboxylic acid (or a salt thereof), carboxybetaine, sulfobetaine, and phosphobetaine.

(Method for Preparing Electrode)

An ascorbic acid responsive electrode according to one embodiment of the present invention is prepared, for example, as follows. A metal layer functioning as an electrode is formed on one side of an insulating substrate. For example, a metal layer having a desired thickness (for example, about 30 nm) is formed by forming a film of a metal material on one side of an insulating substrate film with a predetermined thickness (for example, about 100 μm) by screen printing, physical vapor deposition (PVD, for example sputtering), or chemical vapor deposition (CVD). An electrode layer may also be formed with a carbon material instead of the metal material. Next, a detection layer can be provided on the electrode by coating a solution for preparing a detection layer containing an electron acceptor on the electrode, followed by drying.

An ascorbic acid responsive electrode according to one embodiment of the present invention may be used for a biosensor for measuring the concentration of ascorbic acid contained in a sample.

As described above, in an ascorbic acid-responsive electrode according to one embodiment of the present invention, the dissolving rate of a reagent (particularly an electron acceptor) may be regulated by inclusion of an amino acid, and a saccharide and/or a soluble protein in the detection layer, so that the rate of the oxidation-reduction reaction may be regulated. Namely, it is possible to maintain good linearity in the response current up to a high concentration range of ascorbic acid, and the reproducibility of the measurement results between sensors can be also high.

Although there is no particular restriction on the concentration of ascorbic acid contained in a sample to be measured by the ascorbic acid responsive electrode according to one embodiment of the present invention, it may be 50, 100, 200, 300, 500, 600, 800, or 1,000 mg/dL or more.

There is no particular restriction on a sample insofar as the sample contains a measurement target substance, but it is preferably a biological sample, such as blood, or urine.

(Biosensor)

A biosensor as an ascorbic acid sensor comprises an electrode to serve as a counter electrode together with the ascorbic acid responsive electrode (working electrode) according to one embodiment of the present invention. There is no particular restriction on the counter electrode, insofar as it may be used generally as a counter electrode of a biosensor, and, for example, a carbon electrode made into a film form by screen printing, a metallic electrode made into a film form by physical vapor deposition (PVD, e.g. sputtering), or chemical vapor deposition (CVD), or a silver/silver chloride electrode made into a film form by screen printing may be used.

Further, a three-electrode system may be applied further using a silver/silver chloride electrode, a carbon electrode made into a film form by screen printing, or a metallic electrode made into a film form by physical vapor deposition or chemical vapor deposition as a reference electrode.

When a sample containing ascorbic acid is brought into contact with the surface of an ascorbic acid-responsive electrode (working electrode) according to one embodiment of the present invention, an electron generated by the oxidation reaction of ascorbic acid is transferred to an electron acceptor, so that the acceptor is reduced. Then, by applying an oxidation potential to the working electrode, the reduced electron acceptor is oxidized on the surface of the working electrode, to generate an oxidation current. Based on this current value, the concentration of ascorbic acid in the sample can be measured.

An example of a biosensor according to one embodiment of the present invention will be described below with reference to FIG. 1. Panels A to E are perspective views showing a series of steps of preparing a biosensor. In this regard, a biosensor according to one embodiment of the present invention is not limited to the following embodiment.

As shown in Panel E, the biosensor A comprises a substrate 11, an electrode system constituted with a working electrode 12 having a lead part 12a, and a counter electrode 13 having a lead part 13a, an insulating layer 14, a detection layer 16 containing an electron acceptor, an amino acid and a saccharide and/or a soluble protein, as well as a buffer solution, a spacer 18 having an opening (slit), and a cover 19 having a through-hole 20. As shown in Panel B, a detecting unit 15 is provided on the substrate 11, and the detecting unit 15 is provided with a working electrode 12 and a counter electrode 13 arranged parallel in the width direction of the substrate 11. One ends of both the electrodes are formed to lead parts 12a, 13a, respectively, and these are arranged perpendicular to the other ends in the detecting unit 15 (Panel A). Between the working electrode 12 and the counter electrode 13, there is an insulating part. As shown in Panel B, on the substrate 11 provided with the electrode system, except for the lead parts 12a, 13a and the detecting unit 15, an insulating layer 14 is laminated, and on the detecting unit 15 where the insulating layer 14 is not laminated, a detection layer 16 is laminated. Further, on the insulating layer 14, as shown in Panel D, there is provided a spacer 18 having a narrow opening (slit) extending from an end constituting a sample feed port 17a and covering an area corresponding to the detecting unit 15. Further, on the spacer 18, there is arranged a cover 19 having a through-hole 20 at a position corresponding to the other end of the opening (slit) of the spacer 18 opposite from the feed port (Panel E). In the biosensor A, the empty space portion of the opening (slit), which is enclosed with the detection layer 16, the insulating layer 14, and the cover 19, constitutes a sample supply part 17 with a capillary structure. The sample supply part (capillary) 17 communicates with the outside through an end of the opening (slit) forming the sample feed port 17a, and the through-hole 20. The through-hole 20 works as an air hole for sucking the sample by capillary action. The sample liquid supplied from the sample feed port 17a travels through the sample supply part (capillary) 17 toward the through-hole 20 by capillary action so that an electrode reaction occurs in the detection layer 16.

Such a biosensor may be produced, for example, as follows.

First, as shown in Panel A of FIG. 1, an electrode system comprising a working electrode 12 having a lead part 12a, and a counter electrode 13 having a lead part 13a is formed on a substrate 11.

Subsequently, as shown in Panel B, an insulating layer 14 is formed on the substrate 11, on which the electrode system 12 and 13 has been formed. The insulating layer is formed on the substrate 11 except for lead parts 12a, 13a of the electrodes and a detecting unit 15, in which reagents including an electron acceptor, etc. are applied. The insulating layer 14 may be formed, for example, by printing an insulating paste prepared by dissolving an insulating resin in a solvent on the substrate 11 and subjecting it to a heat treatment or an ultraviolet treatment. Examples of the insulating resin include polyester, a butyral resin, and a phenol resin, and examples of the solvent include carbitol acetate, and a dibasic ester mixed solvent (DBE solvent).

Next, as shown in Panel C, at the detecting unit 15 where the insulating layer 14 is not formed, a detection layer 16 is formed on the substrate 11 and the electrodes 12, 13. The detection layer 16 may be formed, for example, by preparing a dispersion in which an electron acceptor, an amino acid, a saccharide and/or a soluble protein, and a buffer are dispersed, and dispensing the dispersion to the detecting unit 15, followed by drying. As the solvent used for preparing the dispersion, for example, water, a buffer solution, an alcohol, N,N-dimethylformamide (DMF), dimethylsulfoxide (DMSO), etc. may be used.

Next, as shown in Panel D, a spacer 18 is placed on the insulating layer 14. The spacer 18 has an opening in the area corresponding to the detection layer 16. As a material of the spacer 18, for example, a resin film, a tape, or the like may be used. In this regard, in the case of a double-sided adhesive tape, not only adhesion to the insulating film 14 but also to a cover 19 described later may be performed easily. Besides the above, for example, a spacer may be formed by means of resist printing, or the like.

Next, as shown in Panel E, a cover 19 is placed on the spacer 18. The material of the cover 19 is not particularly limited, and, for example, various plastics, etc. may be used. Preferable examples may include a transparent resin such as PET.

The method of using the biosensor A will be described referring to an example in which the sample is whole blood, the measurement target is ascorbic acid, and the electron acceptor is a ruthenium (III) compound.

Firstly, a whole blood sample is brought into contact with the end (sample feed port 17a) of the sample supply part 17 of the biosensor A. Since the sample supply part 17 has a capillary structure as described above, and the through-hole 20 is provided in the cover 19 at a position corresponding to the other end, the sample is sucked inward by capillary action. The sucked sample reaches the surface of the detection layer 16 provided on the detecting unit 15. Then, ascorbic acid in the sample that has reached the surface reacts with the ruthenium (III) compound in the detection layer 16. Specifically, the ruthenium (III) compound is reduced by receiving an electron from ascorbic acid which is the measurement target, to form a ruthenium (II) compound. In this regard, in the detection layer 16, the dissolution rate of the ruthenium (III) compound to a sample solution is regulated by an amino acid and a soluble protein. By applying a positive potential to the electrode, an electron is transferred between the ruthenium (II) compound present in the detection layer 16 and the electrode present under the detection layer 16, so that an oxidation current flow. Based on this current, the concentration of ascorbic acid can be measured.

Specifically, after a lapse of a certain time period from the supply of a whole blood sample, a voltage is applied between the counter electrode 13 and the working electrode 12 by the means for applying a voltage, a reduced ruthenium (II) compound in the detection layer in contact with the electrode is electrochemically oxidized to a ruthenium (III) compound, and the oxidation current at that time is detected via the lead part 12a of the working electrode 12 by a means for measuring the electric signal. Since the value of this oxidation current is proportional to the concentration of ascorbic acid in the sample, the concentration of ascorbic acid in the sample can be determined by converting this value to the concentration of ascorbic acid by the above arithmetic means.

With respect to the voltage to be applied to the working electrode 12, any value is acceptable insofar as it is a positive voltage with respect to the counter electrode, however it is preferably from 10 to 700 mV, from 50 to 500 mV, or from 100 to 400 mV.

A voltage may be applied to the electrode system, after the sample is brought into contact and kept without application of the voltage for a predetermined time period, or a voltage may be applied to the electrode system, as soon as the sample is brought into contact. The keeping time without application of the voltage is, for example, 30 sec or less, or 20 sec or less.

(Apparatus)

Figure 2:
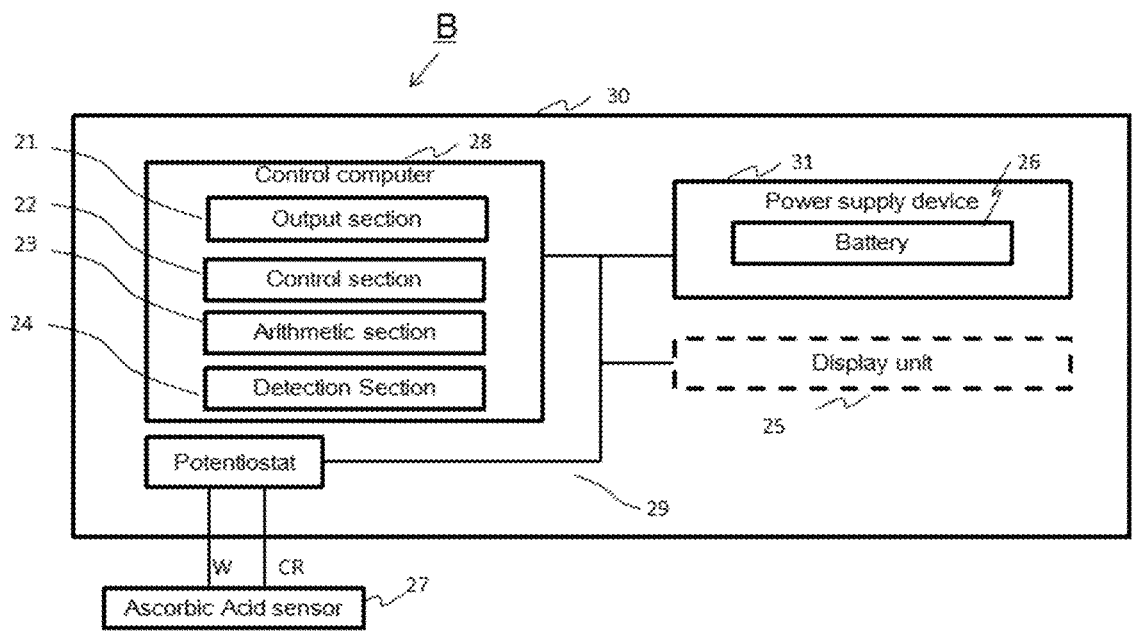
FIG. 2 is a schematic diagram showing one embodiment of a measuring apparatus of the present invention.

Next, a measuring apparatus according to one embodiment of the present invention will be described referring to the drawings. Although an embodiment of the ascorbic acid measuring apparatus is illustrated here, the measuring apparatus according to one embodiment of the present invention is not limited to the following embodiment. FIG. 2 shows a configuration example of main electronic components accommodated in the measuring apparatus B. A control computer 28, a potentiostat 29, and a power supply device 31 are mounted on a substrate 30 which is accommodated in the casing.

In terms of hardware, the control computer 28 includes a processor such as a CPU (Central Processing Unit), a recording medium, such as a memory (RAM (Random Access Memory), or ROM (Read Only Memory)), and a communication unit, wherein the processor loads a program stored in the recording medium (e.g. ROM) on RAM and executes it so that the control computer functions as an apparatus equipped with an output unit 21, a control unit 22, an arithmetic unit 23, and a detection unit 24. In this connection, the control computer 28 may include an auxiliary storage device such as a semiconductor memory (EEPROM, or flash memory), or a hard disk.

The control unit 22 controls the timing of voltage application, an applied voltage value, and the like.

The power supply device 31 has a battery 26 and supplies power for operation to the control computer 28 and the potentiostat 29. In this regard, the power supply device 31 may also be placed outside the casing.

The potentiostat 29 is a device that makes the potential of the working electrode constant with respect to the reference electrode; applies a predetermined voltage between the counter electrode and the working electrode of the ascorbic acid sensor 27 as controlled by the control unit 22, and using terminals CR, W; measures the response current of the working electrode obtained by the terminal W; and sends the measured result to the detecting unit 24.

The arithmetic unit 23 calculates the concentration of a measurement target substance from the detected current value and stores it. The output unit 21 performs data communication with the display unit 25, and transmits the calculation result of the concentration of the measurement target substance by the arithmetic unit 23 to the display unit 25. For example, the display unit 25 can display the calculation result of the concentration of ascorbic acid received from the measuring apparatus B on a display screen in a predetermined format.

Figure 3:
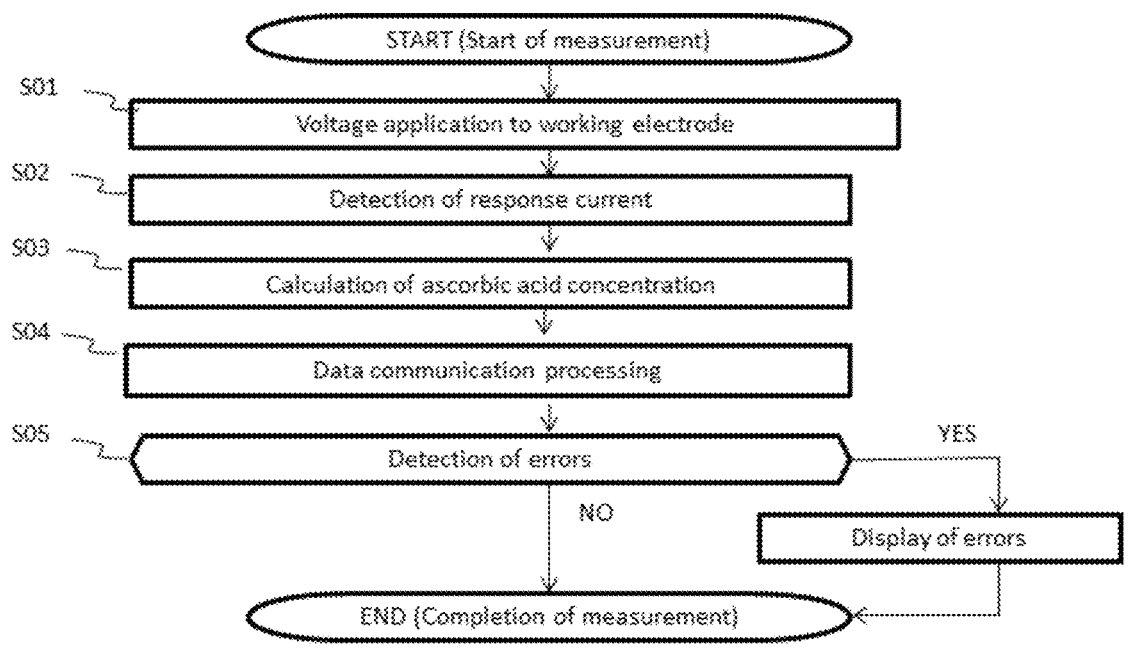
FIG. 3 is a flow chart showing one embodiment of a measuring program using a measuring apparatus of the present invention.

FIG. 3 is a flowchart showing an example of a measurement process for the concentration of ascorbic acid by the control computer 28. Upon receipt of an instruction to start a measurement of the concentration of ascorbic acid, by the CPU (control unit 22) of the control computer 28, the control unit 22 controls the potentiostat 29 to apply a predetermined voltage to the working electrode, and to start measuring the response current from the working electrode (step S01). The detection of attachment of the sensor to the measuring apparatus may be used as an instruction to start a measurement of the concentration.

Next, the potentiostat 29 measures a response current obtained by applying a voltage, namely, a charge transfer rate-determining current based on the transfer of electrons derived from a measurement target substance (ascorbic acid) in a sample to the electrode, such as a steady current 1 to 20 sec after the voltage application, and sends it to the detecting unit 24 (step S02).

The arithmetic unit 23 performs arithmetic processing based on the current value to calculate the concentration of ascorbic acid (step S03). For example, the arithmetic unit 23 of the control computer 28 holds in advance a calculation formula of the concentration of ascorbic acid, or calibration curve data between the current value and the concentration of ascorbic acid, and calculates the concentration of ascorbic acid using the formula or the calibration curve.

The output unit 21 transmits the calculation result of the concentration of ascorbic acid to the display unit 25 via the communication link established with the display unit 25 (step S04). Thereafter, the control unit 22 checks the presence or absence of a measurement error (step S05), finishes the measurement if an error is not detected, and displays the concentration of ascorbic acid on the display unit. If an error is recognized, after displaying an error message, the processing by the flow in FIG. 3 is ended. Further, it is also possible to store the calculation result in the arithmetic unit 23, and call up the calculation result later for displaying it on the display unit for confirmation. In this case, checking for measurement error (step S05) by the control unit 22 is performed after the transmittance of the calculation result to the display unit 25 (step S04), but the order of these steps may be reversed.

EXAMPLES

The embodiments of the invention will be described below more specifically with reference to Examples, but the embodiments of the invention are not limited to the following embodiments.

Example 1

As shown in FIG. 1, a biosensor was produced by the following procedures. First, as shown in Panel A, a PET substrate (50 mm long, 6 mm wide, and 250 µm thick) was prepared as an insulating substrate 11 of the ascorbic acid sensor, and on one side of the same a carbon electrode system constituted with a working electrode 12 and a counter electrode 13 having respectively a lead part was formed by screen printing.

Next, as shown in Panel B, an insulating layer 14 was formed on the electrodes. First, a polyester insulating resin was dissolved in a carbitol acetate solvent up to 75% (wt) to prepare an insulating paste, which was screen-printed on the electrodes. As for the printing conditions, the screen was 300 mesh, the squeegee pressure was 40 kg, and the printed amount was 0.002 mL per 1 $cm^2$ of electrode area. The screen printing was performed except for the detecting unit 15, and the lead parts 12a, 13 a. Thereafter, a heat treatment was performed at 155° C. for 20 min to form an insulating layer 14.

Further, as shown in Panel C, a ruthenium compound layer (detection layer) 16 was formed on the detecting unit 15 where the insulating layer 14 was not formed. First, a ruthenium compound solution (pH 7.5) containing 2.9% (wt) of a ruthenium compound ([$Ru(NH_3)_6$]$Cl_3$, produced by Heesung Metal Ltd.), 5.0% (wt) of taurine, 2.4% (wt) of NPS (TOYOBO CO., LTD.), CHAPS, 2-propanol, and distilled water was prepared. Into the detecting unit 15, 1.0 µL of the ruthenium compound liquid was dispensed. The amounts of reagents contained in the detection layer per sensor are shown in Table 1.

The surface area of the detecting unit 15 was about 0.02 $cm^2$, and the surface area of the electrodes 12, 13 in the detecting unit 15 was about 0.003 $cm^2$, respectively. Then, this was dried at 25° C. to form a ruthenium compound layer 16.

As shown in Panel D, a spacer 18 having an opening was placed on the insulating layer 14.

Further, as shown in Panel E, a cover 19 having a through-hole 20 serving as an air hole was placed on the spacer 18 to fabricate a biosensor. Since the empty space of the opening portion of the spacer 18 enclosed between the cover 19 and the insulating layer 14 had a capillary structure, it was used as the sample supply part 17. The biosensor fabricated in this way was used as the biosensor 1 of Example.

Further, a biosensor of Comparative Example was prepared in the same manner except that taurine and NPS in the biosensor 1 were replaced with distilled water.

TABLE 1

| Reagents per sensor | Comparative Example | Example |
|---|---|---|
| CHAPS | 0.25 µg | 0.25 µg |
| Distilled Water | 531.80 µg | 487.52 µg |
| Ruthenium | 17.60 µg | 17.60 µg |

TABLE 1-continued

| Reagents per sensor | Comparative Example | Example |
|---|---|---|
| 2-Propanol | 50.34 μg | 50.34 μg |
| Taurine | — | 30.00 μg |
| NPS | — | 14.29 μg |

Next, ascorbic acid-containing whole blood samples having a hematocrit (Ht) value of 42%, and containing ascorbic acid (ASA) at a predetermined concentration (for Example, 0, 140, 280, 490, 560, 840, 1120, or 1400 mg/dL, and for Comparative Example 0, 50, 100, 200, 300, 400, 600, 800, or 1000 mg/dL) were prepared.

Figure 4:
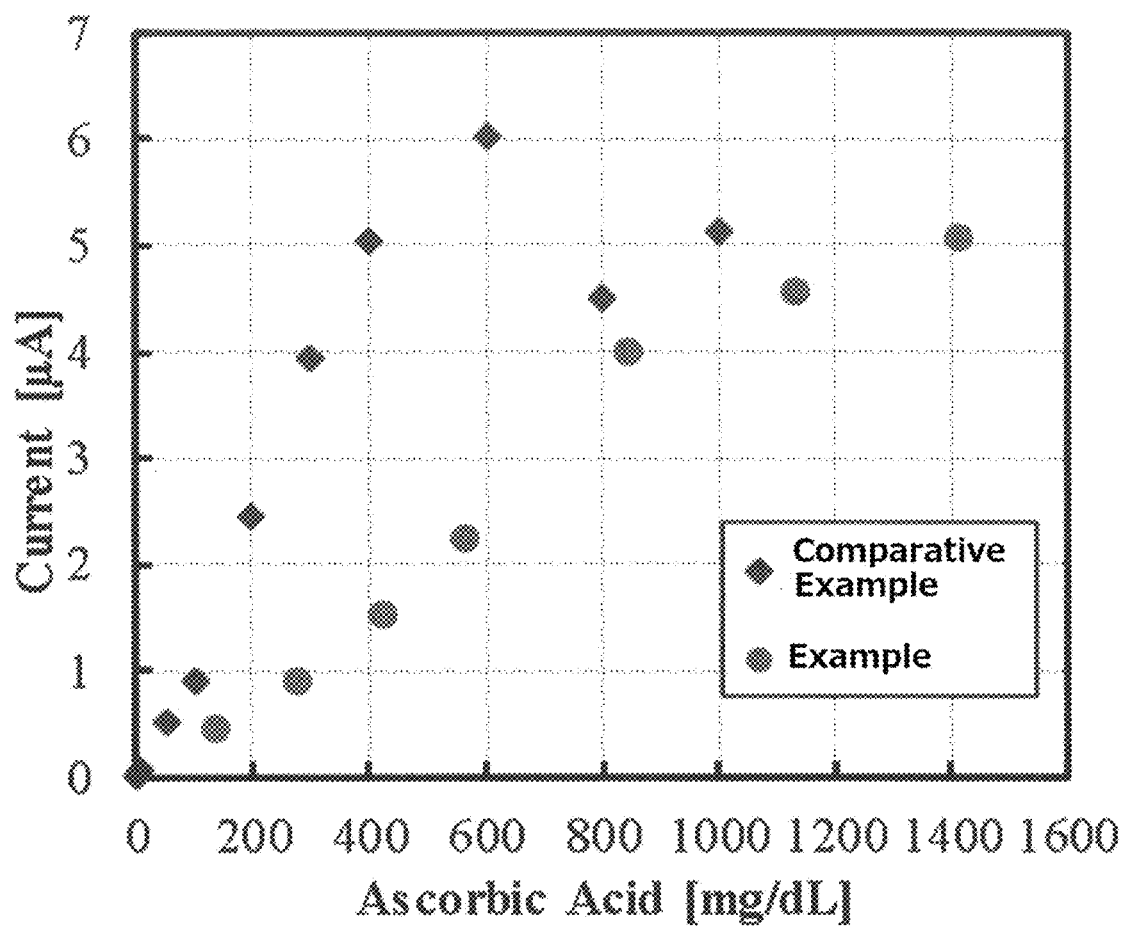
FIG. 4 is a graph showing response current values when samples containing various concentrations of ascorbic acid are reacted with a biosensor of Example or Comparative Example and a voltage is applied thereto.

Each of the ascorbic acid-containing whole blood samples was supplied from the sample supply part of the biosensor and reacted. Then a current value was measured by chronoamperometry. The measurement sequence was as follows: open circuit 20 sec→200 mV, 20 sec (end point measurement). The results are shown in FIG. 4. It was found that, when the biosensor 1 of Example was used, a current profile in which the response current increased in accordance with increase in the ascorbic acid concentration over the entire concentration range measured was obtained. On the other hand, when the biosensor of Comparative Example was used, a current profile in which the response current increased in accordance with increase in the ascorbic acid concentration was obtained in a low concentration range (400 mg/dL or less), however, in a high concentration range (600 mg/dL or more), sufficiently good linearity was not obtained between the ascorbic acid concentrations and the response current values.

By adding taurine and NPS, the dissolution rate of reagents (especially a ruthenium compound) could be reduced. In other words, it was found that the oxidation-reduction reaction rate could be controlled, and as a result, good linearity could be maintained up to a high ascorbic acid concentration range of 600 mg/dL or more.

While whole blood was used in the above measurement of ascorbic acid, there exist reducing substances, such as uric acid, or glutathione in whole blood. According to the embodiments of the present invention, even in the presence of the reducing substance, measurement of ascorbic acid is possible in a wide concentration range, and it has been found there is specificity of measurement under these measurement conditions.

Figure 5:
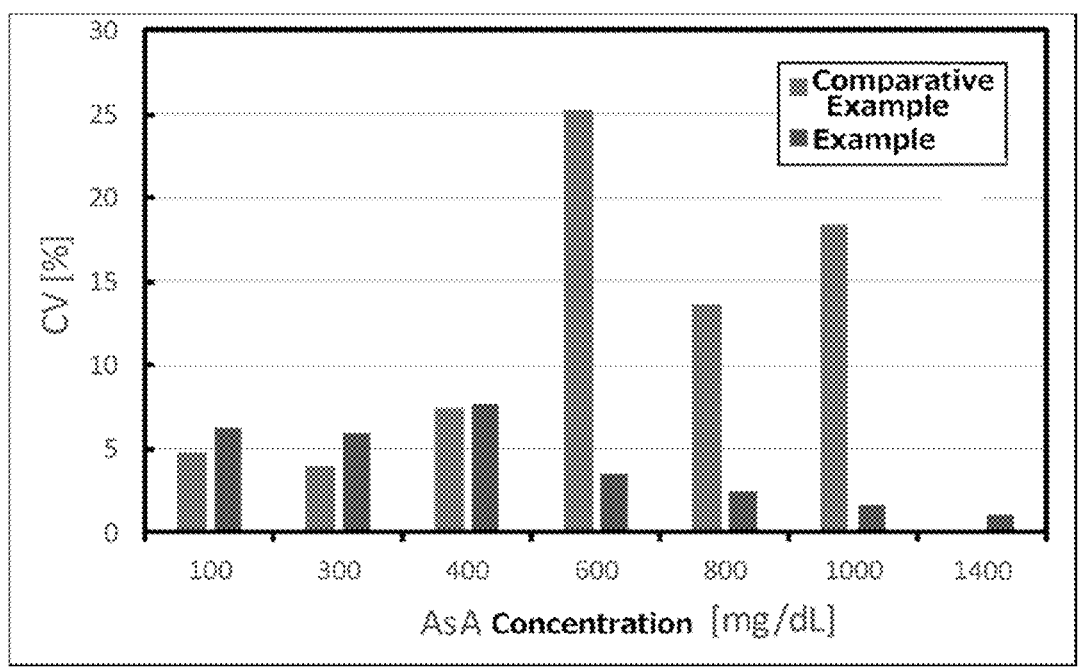
FIG. 5 is a graph showing the reproducibility of a biosensor of Example or Comparative Example at the time of measurements of samples containing various concentrations of ascorbic acid.

Further, using an ascorbic acid-containing whole blood sample having an ascorbic acid concentration 100 to 1400 mg/dL (100 to 1000 mg/dL for Comparative Example), the reproducibility (CV) (%) in n=5 was calculated according to CV=SD/Ave. The results are shown in Table 2 and FIG. 5. When the biosensor 1 of Example was used, it was found that adequate reproducibility was obtainable over the entire concentration range measured. On the other hand, when the biosensor of Comparative Example was used, adequate reproducibility was obtained in the low concentration range (400 mg/dL or less), but in the high concentration range (600 mg/dL or more) adequate reproducibility could not be obtained.

It was found that by adding an amino acid and NPS which was a soluble protein, the dissolution rates of a reagent between sensors became uniform, and as a result, the reproducibility in the high concentration range was improved.

TABLE 2

| | 100 mg/dL | 300 mg/dL | 400 mg/dL | 600 mg/dL | 800 mg/dL | 1000 mg/dL | 1400 mg/dL |
|---|---|---|---|---|---|---|---|
| Comparative Example | 4.88% | 3.96% | 7.49% | 25.25% | 13.62% | 18.39% | — |
| Example | 6.26% | 5.97% | 7.72% | 3.49% | 2.51% | 1.71% | 1.13% |

Figure 6:
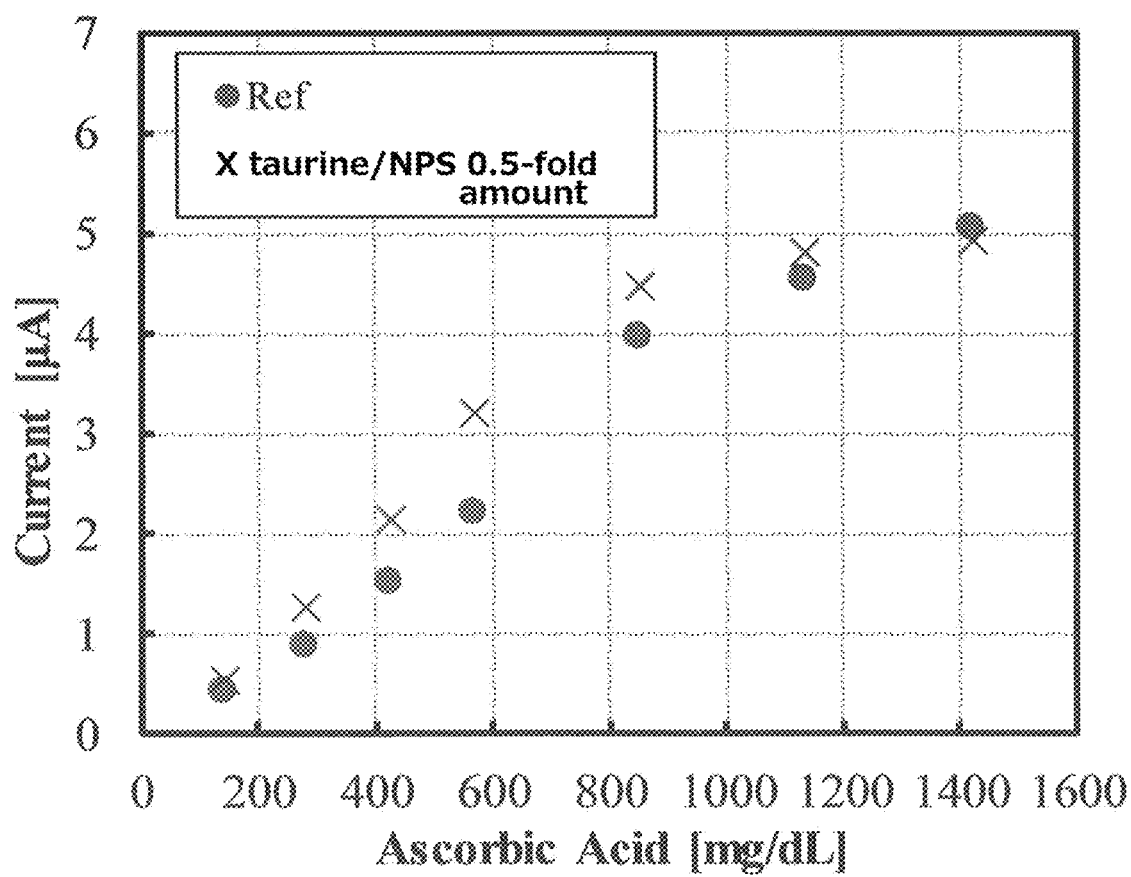
FIG. 6 is a graph showing response current values when samples containing various concentrations of ascorbic acid are reacted with a biosensor of Example containing different concentrations of an amino acid and a soluble protein, and a voltage is applied thereto.

The biosensor 2 was fabricated in the same manner, except that the amounts of taurine and NPS were respectively changed to be 0.5 times as high as in the biosensor 1. Using the biosensor 1 and the biosensor 2, the current values were measured for the respective ascorbic acid-containing whole blood samples in the same manner as described above. The results are shown in FIG. 6. Both the biosensor 1 and the biosensor 2 showed good linearity between the concentrations of ascorbic acid and the response current values, but the biosensor 1 exhibited an improved linearity property. Namely, it was more preferable that the concentration of taurine in the electrode reagent was from about 4.5 to 5.0%, and the content of NPS to be added was from about 2.4 to 2.5%.

Example 2

Figure 7:
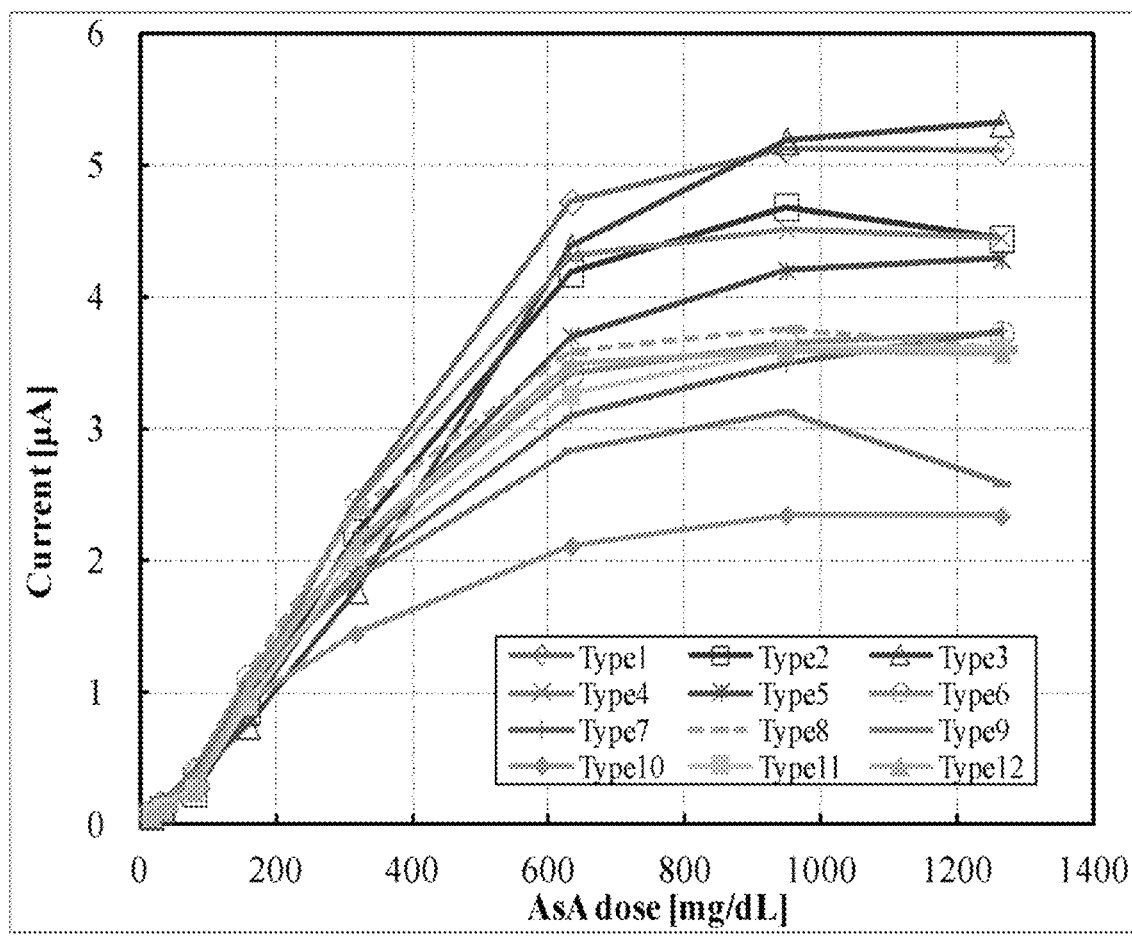
FIG. 7 is a graph showing response current values when samples containing various concentrations of ascorbic acid are reacted with a biosensor of Example containing various concentrations of various amino acids and various concentrations of a soluble protein, and a voltage is applied thereto.

A biosensor was fabricated in the same manner, except that the amino acid in the biosensor 1 was changed to the amino acid(s) at the content(s) set forth in Table 3, and NPS was changed to the content set forth in Table 3. Using the biosensor, the current values for the respective ascorbic acid-containing whole blood samples were measured in the same manner as described above. The results are shown in FIG. 7. It was found that the linearity was improved, even when an amino acid other than taurine was used. In addition, it was found that as the addition amounts of an amino acid and NPS were increased, good linearity was exhibited up to an ultrahigh concentration range).

TABLE 3

| | Additive | | | | |
|---|---|---|---|---|---|
| Type | Taurine | L-α-Alanine | Glycine | Serine | NPS |
| 1 | 2.50% | — | — | — | 1.19% |
| 2 | 3.75% | — | — | — | 1.19% |
| 3 | 5.00% | — | — | — | 2.38% |
| 4 | 1.25% | 1.25% | — | — | 1.19% |
| 5 | 2.50% | 2.50% | — | — | 2.38% |
| 6 | 1.25% | 1.25% | — | — | 1.79% |
| 7 | 1.25% | 1.25% | — | — | 2.38% |
| 8 | — | — | — | 2.50% | 1.19% |
| 9 | — | — | — | 3.75% | 1.19% |
| 10 | — | — | — | 5.00% | 1.19% |
| 11 | 2.50% | 0.63% | 0.63% | — | 1.19% |
| 12 | 3.75% | 0.63% | 0.63% | — | 1.19% |

Example 3

Figure 8:
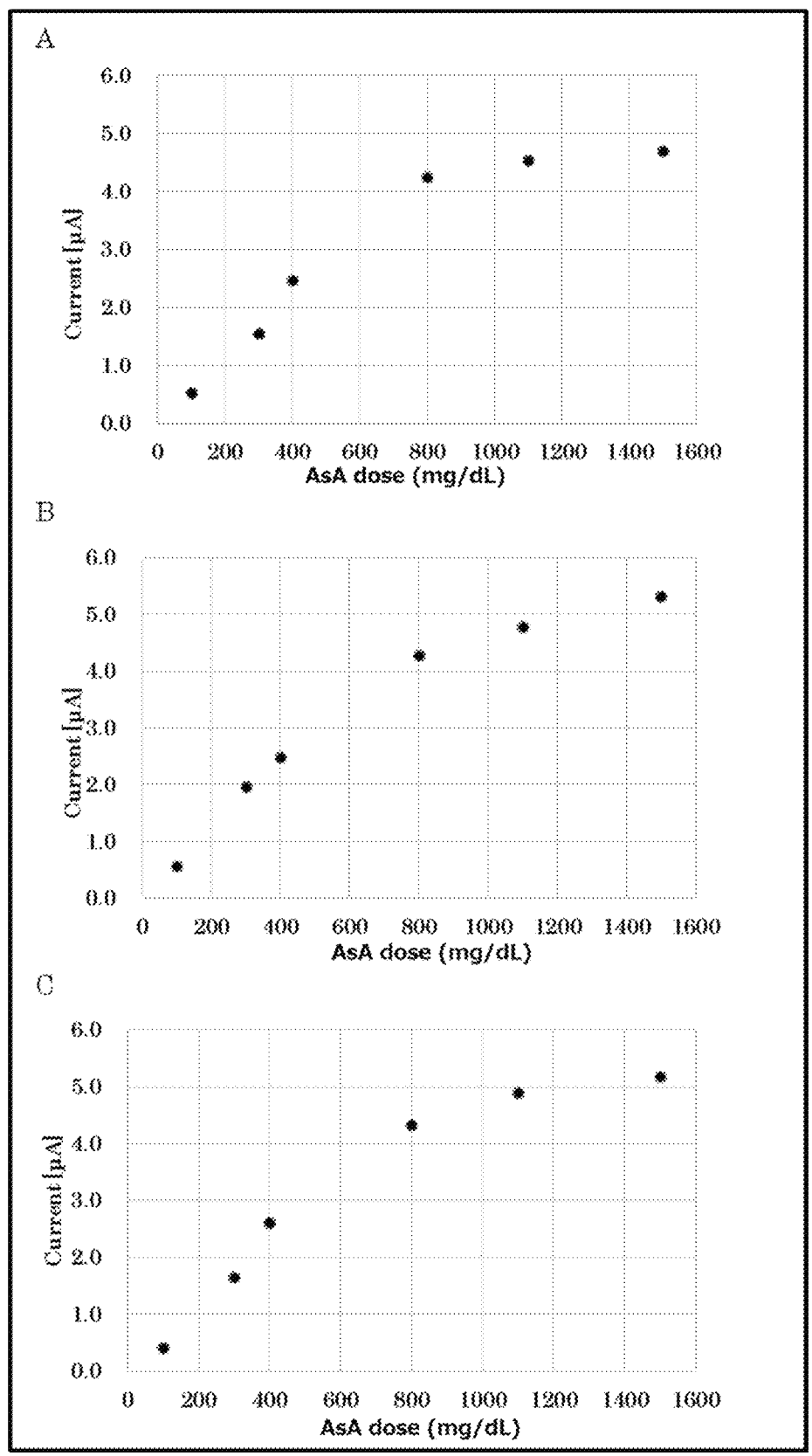
FIG. 8 is a graphs showing response current values when samples containing various concentrations of ascorbic acid are reacted with a biosensor of Example containing an amino acid, and a saccharide or a soluble protein, and a voltage is applied thereto. Panel A shows the results using a biosensor of Example containing taurine (5%) and xylitol (2.38%). Panel B shows the results using a biosensor of Example containing taurine (5%) and trehalose (2.38%). Panel C shows the results using a biosensor of Example containing taurine (5%) and BSA (bovine serum albumin) (2.38%).

A biosensor was fabricated in the same manner except that NPS in the biosensor 1 was changed to BSA or a saccharide (xylitol, or trehalose). Using the biosensor, the current values for the respective ascorbic acid-containing whole blood samples were measured in the same manner as described above. The results are shown in FIG. 8.

It was found that good linearity was obtained between the concentrations of ascorbic acid and the response current values even when a saccharide (xylitol, or trehalose) was used together with an amino acid. It was also found that even when BSA was used as a soluble protein, good linearity was obtained between the concentrations of ascorbic acid and the response current values.

REFERENCE SIGNS LIST

A Biosensor
11 Substrate
12 Working Electrode
12a Lead Part
13 Counter Electrode
13a Lead Part
14 Insulating Layer
15 Detecting Unit
16 Detection Layer
17 Sample Supply Part (Capillary)
17a Sample Feed Port
18 Spacer
19 Cover
20 Trough Hole
B Measuring Apparatus
21 Output Unit
22 Control Unit
23 Arithmetic Unit
24 Detecting Unit
25 Display Unit
26 Battery
27 Ascorbic Acid Sensor
28 Control Computer
29 Potentiostat
30 Substrate
31 Power Supply Device
CR, W Terminal
S01 to S05 Each Step in Measurement Process for Ascorbic Acid Concentration While the invention has been described in detail with reference to exemplary embodiments thereof, it will be apparent to one skilled in the art that various changes may be made, and equivalents employed, without departing from the scope of the invention. Each of the aforementioned documents as well as JP2017-205759 is incorporated by reference herein in its entirety.

What is claimed is:

1. An ascorbic acid responsive electrode comprising
an electrode, and
a detection layer comprising
a non-catalytic electron acceptor that receives an electron from ascorbic acid,
an amino acid, and
a saccharide and/or a soluble protein;
wherein, in the detection layer, the electron acceptor is reduced by the ascorbic acid, and the reduced electron acceptor is oxidized at the electrode.

2. The ascorbic acid responsive electrode according to claim 1, wherein the electron acceptor is a ruthenium compound.

3. The ascorbic acid responsive electrode according to claim 2, wherein the ruthenium compound is a ruthenium (III) complex represented by the following chemical Formula:

$$[Ru(NH_3)_5X]^{n+},$$

wherein X represents $NH_3$, a halogen, CN, pyridine, nicotinamide, bipyridine, or $H_2O$; and $^{n+}$ represents the valence of the ruthenium (III) complex.

4. The ascorbic acid responsive electrode according to claim 1, wherein the amino acid is selected from the group consisting of taurine, alanine, glycine, and serine.

5. The ascorbic acid responsive electrode according to claim 1, wherein the soluble protein is selected from the group consisting of Neo Protein Saver, and serum albumin.

6. The ascorbic acid responsive electrode according to claim 1, wherein the saccharide is selected from the group consisting of xylitol, and trehalose.

7. A biosensor comprising
a substrate, and
the ascorbic acid responsive electrode according to claim 1, and a counter electrode, which are provided on the substrate.

8. A method for measuring the concentration of ascorbic acid, comprising reacting a sample containing ascorbic acid with the biosensor according to claim 7, applying an oxidation potential to the ascorbic acid responsive electrode to measure a response current, and calculating the concentration of ascorbic acid based on the response current.

9. The method according to claim 8, wherein said sample has the concentration of ascorbic acid of 50 mg/dL or more.

10. The method according to claim 8, wherein the concentration of ascorbic acid is calculated based on a calibration curve between the response current value and the concentration of ascorbic acid.

11. An apparatus for measuring the concentration of ascorbic acid comprising the biosensor according to claim 7;
a control unit for controlling voltage application to the biosensor;
a detecting unit for detecting an ascorbic acid response current generated by applying a voltage to the biosensor;
an arithmetic unit for calculating the concentration of ascorbic acid from the current value; and
an output unit for outputting the calculated concentration of ascorbic acid.

* * * * *